United States Patent
Swanson (10) Patent No.: US 6,814,731 B2
(45) Date of Patent: Nov. 9, 2004

(54) METHODS FOR RF ABLATION USING JET INJECTION OF CONDUCTIVE FLUID

(75) Inventor: David K. Swanson, Campbell, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 52 days.

(21) Appl. No.: 10/154,011

(22) Filed: May 20, 2002

(65) Prior Publication Data

US 2003/0216722 A1 Nov. 20, 2003

(51) Int. Cl.[7] ............................................. A61B 18/14
(52) U.S. Cl. ........................... 606/32; 606/34; 606/41
(58) Field of Search ............................. 606/41, 32, 34

(56) References Cited

U.S. PATENT DOCUMENTS

| 5,334,193 A | 8/1994 | Nardella |
| 5,342,357 A | 8/1994 | Nardella |
| 5,348,554 A | 9/1994 | Imran et al. |
| 5,383,876 A | 1/1995 | Nardella |
| 5,423,811 A | 6/1995 | Imran et al. |
| 5,658,278 A | 8/1997 | Imran et al. |
| 5,697,927 A | 12/1997 | Imran et al. |
| 5,718,701 A | 2/1998 | Shai et al. |
| 6,010,500 A * | 1/2000 | Sherman et al. ............... 606/41 |
| 6,030,379 A | 2/2000 | Panescu et al. |
| 6,217,574 B1 | 4/2001 | Webster |
| 6,241,666 B1 | 6/2001 | Pomeranz et al. |
| 2002/0183738 A1 * | 12/2002 | Chee et al. .................... 606/41 |
| 2003/0212394 A1 * | 11/2003 | Pearson et al. ................ 606/41 |

* cited by examiner

Primary Examiner—Lee S. Cohen
(74) Attorney, Agent, or Firm—Bingham McCutchen LLP (57) ABSTRACT

A method of preparing and ablating heart tissue includes a pre-treatment step of delivering a jet of conductive fluid to a portion of heart tissue. The conductive fluid is delivered using an injection device such as a hand-held jet injector, probe, or catheter. After injecting the heart tissue with the conductive fluid, RF energy is delivered to the site of the injection to form a lesion. The method enables a physician to produce large and accurately placed lesions within the treated tissue.

25 Claims, 11 Drawing Sheets

METHODS FOR RF ABLATION USING JET INJECTION OF CONDUCTIVE FLUID

FIELD OF THE INVENTION

The present invention relates generally to the field of radio frequency (RF) ablation of tissue, and, more specifically, to devices and methods for the neddleless injection of a conductive fluid into tissue prior to and in conjunction with RF ablation.

BACKGROUND OF THE INVENTION

RF ablation techniques destroy tissue by heating. Typically, high frequency alternating current flows from one or more electrodes into the tissue, producing ionic agitation in the tissue about the electrode area as the ions attempt to follow the direction changes of the alternating current. The agitation eventually drives water from the cells leading to desiccation and coagulation, thereby creating a lesion in the tissue. There are generally two forms of heating that lead to lesion formation in RF ablated tissue. The first is primary heating (direct) of tissue via the interaction of the tissue with the alternating current of the RF electrode. Tissue is also heated by secondary heating (indirect) via conductive heating from the areas heated by the RF energy. The size of the lesion depends on several factors including the amount of RF power delivered to the tissue, the amount of time the RF electrode is energized, as well as resistivity of the tissue (which can change as the tissue is coagulated).

RF ablation techniques are currently used to form lesions in a variety of organ and tissue types. For example, RF ablation has been used to form lesions in cancerous lung and liver tissue. One other important area where RF ablation is used relates to the treatment of cardiac arrhythmia. The heart includes a number of normal electrical pathways which are responsible for the propagation of electrical signals from the upper to lower chambers necessary for performing normal systole and diastole function. The presence of arrhythmogenic site or accessory pathway can bypass or short circuit these normal pathways, potentially resulting in very rapid heart contractions, typically referred to as tachycardias. Treatment is accomplished by ablating the abnormal arrythmogenic tissue or accessory pathway responsible for the tachycardia. RF ablation is a standard treatment for supraventricular tachycardia (SVT) such as antrioventricular nodal reentry tachycardia (AVNRT) and accessory pathways. RF ablation is also used in the treatment of ventricular tachycardia (VT) and atrial fibrillation (AF).

Current RF technologies deposit most of their delivered RF energy to within about 2 mm of tissue adjacent to where the ablation electrode is placed. Lesion depth is extended by thermal conduction (secondary heating) to deeper tissue layers over time. The maximum safe RF power that can be delivered is limited by the need to keep the maximum tissue temperature below 100° C. If tissue temperature exceeds 100° C., an explosive release of steam can erupt that could cause harmful and unwanted perforations in the tissue. Consequently, the maximum lesion depth that can be created using RF ablation devices that are not actively cooled is around 4–5 mm.

When an actively cooled RF ablation device is used, RF power can be increased as compared to non-cooled RF devices without exceeding the maximum tissue temperature of 100° C. Ablation using cooled RF electrodes can result in lesion depths of 8–10 mm. However, a disadvantage of cooling the RF electrodes is that this exterior cooling does not greatly effect tissue temperature more than about 2 mm below the surface. While temperatures may be within acceptable limits at the surface, temperatures below the surface may exceed safety margins. Since the hottest tissue temperatures are located 1–3 mm below the surface, control of RF power to safe levels using active cooling is difficult.

Another technique that has been used to create deeper lesions is the irrigation and pumping of a saline solution directly into the tissue to be ablated. The irrigation is typically accomplished using hollow electrode needle-type structures that have holes drilled therein that allow saline solution to exit into the tissue of interest. These same needle-type structures are also used to deliver the RF energy during ablation. The injection of conductive fluid decreases electrical resistance (i.e., reduces ohmic losses) and thus permits the tissue to carry more energy without exceeding the 100° C. upper temperature limit. The difficulty with this method lies in the unpredictability of the fluid transfer. Moreover, prior art devices typically delivery saline solutions at relatively low pressures, relying on the migration of the saline fluid through the extracellular space. Consequently, it is sometimes difficult to produce deep penetration of saline solution over a specific portion of the tissue of interest.

For example, experimental results using injection by needle of dyed saline solution indicate that injectate tends to flow in between tissue layers and could orient current in unexpected directions from the injection site. The conductive fluid, in other words, does not reliably go in a consistent pattern thus making a predictable and precise ablation of tissue ablation very difficult. Because of the unpredictable nature of injection of a conductive fluid via a needle, this is not an optimum approach in the treatment of a disease such as cardiac arrhythmia (i.e., in treatments where precision is important).

It is desirable, therefore, to improve RF ablation techniques so that deeper lesions can be created of a predictable size while at the same time keeping tissue temperatures below 100° C. throughout the lesion area. As will be described in more detail below, the present invention provides improved lesion creation such that it achieves these and other desired results, which will be apparent from the description below to those skilled in the art.

SUMMARY OF THE INVENTION

In a first aspect of the invention, a method for preparing heart tissue for RF ablation includes the steps of providing an injection device adjacent to a portion of the heart tissue and injecting the tissue with a jet of conductive fluid to a depth within the range of about 2 mm to about 5 mm.

In a second aspect of the invention, a method for ablating heart tissue comprises the steps of providing an injector device adjacent to a portion of the heart tissue the injector device including a plurality of ports and a plurality of electrodes, injecting the heart tissue with a jet of conductive fluid from the injector device, and applying RF energy to the heart tissue containing the injected conductive fluid using the electrode so as to form a lesion.

In yet another aspect of the invention, a method of forming a lesion within heart tissue includes the steps of providing access to the heart of a patient, injecting a portion of the heart tissue with a jet of conductive fluid to a depth within the range of about 2 mm to about 5 mm, and ablating at least some of the tissue injected with the jet of conductive solution using RF ablation.

In still another aspect of the invention, a device is disclosed for injecting conductive solution into heart tissue.

The device includes a source of pressurized gas, a syringe having at least one nozzle at one end thereof, the source of pressurized gas being in fluid communication with a plunger contained within the syringe. A conductive fluid is stored within the syringe. A switch is provided for releasing a pressurized gas from the source into the syringe so as to cause the device to deliver a jet of conductive fluid at a speed sufficient to penetrate heart tissue to a depth within the range of about 2 mm to about 5 mm.

In still another aspect of the invention, an RF ablation probe includes a handle, a shaft attached to the handle, and a distal section having a lumen therethrough, the distal section including a plurality of ports oriented on one side of the distal section, the distal section further including a plurality of RF electrodes, and a source of pressurized conductive fluid connected to the lumen of the probe.

In yet another aspect of the invention, a RF catheter includes a handle, a shaft attached to the handle, and a distal segment having a lumen therethrough, the distal segment including a plurality of ports oriented on one side of the distal section, the distal segment further including a plurality of RF electrodes, and a source of pressurized conductive fluid connected to the lumen of the catheter.

It is an object of the invention to provide a method for pre-treating tissue prior to RF ablation. It is a further object of the invention to provide a method that reduces the effective resistivity of tissues and thereby reduce power dissipation in those same tissues. Another object of the invention is to provide an improved RF ablation method that can form accurate and deep lesions within tissue. Another object of the invention is to proved a combination injection device/RF ablation device. The combined device can take the form of a probe or a catheter. These and other objects of the invention are described in detail below.

DETAILED DESCRIPTION OF THE PREFERRED EMBODIMENTS

Figure 1:
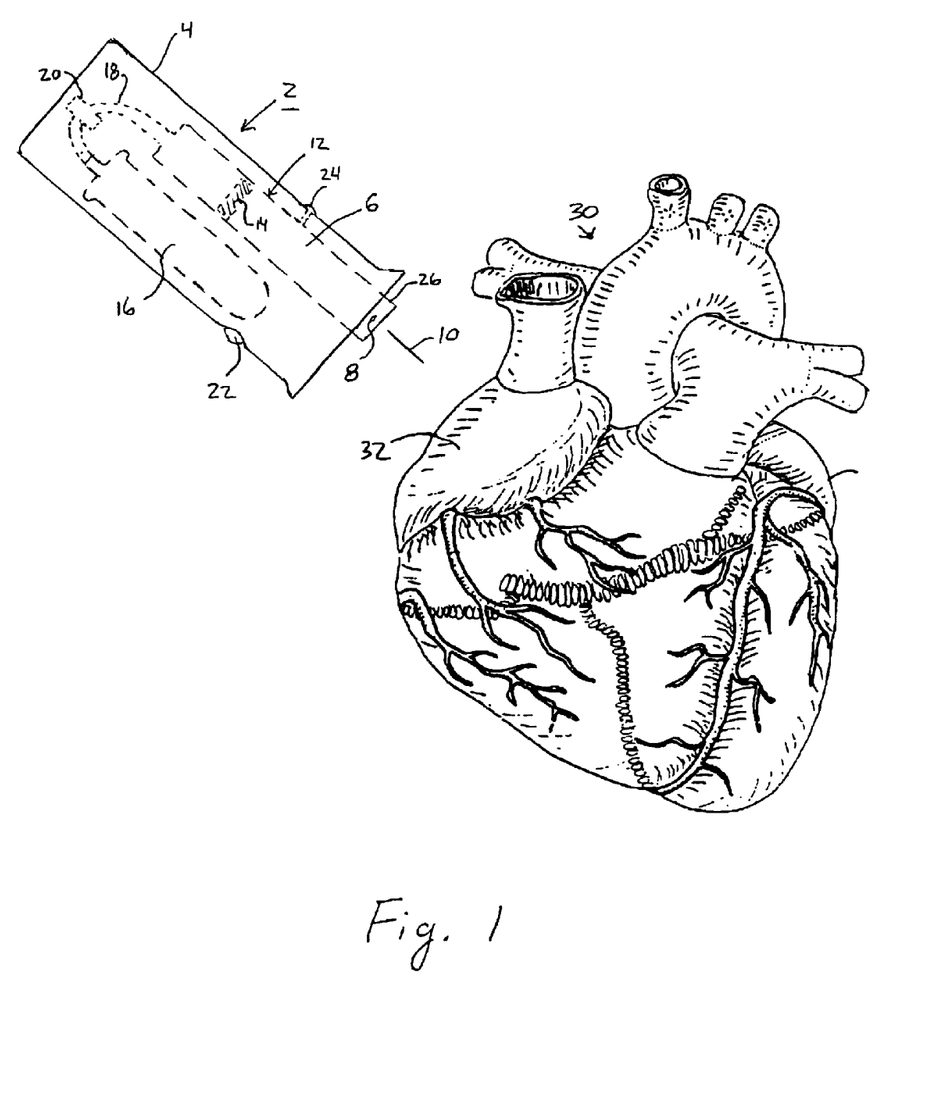
FIG. 1 is a diagram illustrating a needleless hand-held jet injector for pre-treating tissue such as heart tissue prior to performing RF ablation.

Referring to FIG. 1, a hand-held jet injector 2 is shown in accordance with one preferred embodiment of the present invention. The hand-held jet injector 2 is used to pre-treat tissue prior to the delivery of RF energy. The hand-held jet injector 2 includes a body portion 4 which is handled by an operator. The hand-held jet injector 2 contains a conductive fluid 6 therein that is ejected out one or more nozzles 8 to form a narrow jet 10 of conductive fluid 6 that is able to penetrate the tissue of a patient. Preferably, the tissue is heart tissue.

In one preferred aspect of the invention, the conductive fluid 6 is stored in a syringe-like structure 12 that includes a plunger 14 that is moved to eject the conductive fluid 6 (i.e., the injectate) outside the hand-held injector 2. In FIG. 1, the syringe-like structure 12 is preferably pneumatically connected to a source of pressurized gas 16 via a conduit 18. The pressurized gas 16 may include, for example, a pressurized $CO_2$ container although other gases may be employed. The pressurized gas 16 communicates with the portion of the syringe-like structure 12 that is not in contact with the conductive fluid 6. In this regard, the plunger 14 separates the pressurized gas from the conductive fluid 6. A valve 20 is preferably located between the syringe-like structure 12 and the source of pressurized gas 16. The valve 20 is preferably controlled either mechanically or electrically by a switch 22 that is accessible on the body portion 4 of the hand-held jet injector 2. Activation of the switch 22 causes ejection of a narrow jet 10 of conductive fluid 6.

The hand-held jet injector 2 may eject a pre-determined volume of conductive fluid 6 with each press of the switch 22. Alternatively, the hand-held jet injector 2 may eject a narrow jet 10 of conductive fluid 6 for as long a time as the switch 22 is depressed. FIG. 1 also shows a refill port 24 that can be used to load the hand-held jet injector 2 with conductive fluid 6. In an alternative embodiment, the hand-held jet injector 2 may be coupled to a separate source of pressurized gas 16 such as a tank or wall supply (not shown). Similarly, the hand-held jet injector 2 may also be connected to an external source of conductive fluid 6 (not shown) through appropriate tubing or the like. In this manner, the pumping mechanism and conductive fluid 6 may be provided external to the body portion 4 of the hand-held jet injector 2.

The hand-held jet injector 2 uses relatively high pressures to form the narrow jet 10 of conductive fluid 6. Preferably, pressures in the range of about 500 psi to about 1500 psi are used. The amount of pressure depends on the desired depth of penetration and the type of tissue that is being treated. Preferably, the hand-held jet injector 2 produces a narrow jet 10 of conductive fluid 6 at a sufficient speed to penetrate heart tissue to a depth within the range of about 2 mm to about 5 mm. For example, fatty tissue is relatively easy to penetrate and would require lower pressures than muscle tissue. It is preferable that the operator can control the pressure that is delivered via the hand-held jet injector 2. This pressure can be input to the device using commonly known mechanical or electronic control techniques.

In a preferred embodiment of the invention, the hand-held jet injector 2 is used to pre-treat human heart tissue 32 prior to RF ablation for the treatment of tachycardia. The tachycardia treatment is performed, in one aspect of the invention, after a surgical operation such as a median sternotomy is performed to allow access to the surface of a human heart 30. After access to the heart 30 has been established, the next step employs the hand-held jet injector 2 to prepare the heart tissue by injecting the tissue with a narrow jet 10 of conductive fluid 6. Injection is preferably accomplished by resting a collar 26 of the hand-held jet injector 2 adjacent to the tissue of interest. Importantly, there are no needles that penetrate the heart tissue 32. It should be understood that injection does not necessarily require holding the hand-held jet injector 2 against the heart tissue 32. Depending on the type of hand-held jet injector 2 used, it may be possible to inject the heart tissue 32 by holding the hand-held jet injector 2 some distance away from the surface of the heart tissue 32.

Some procedures may require a single burst or a single sustained injection of conductive fluid 6. In other procedures, however, it may be advantageous to inject the heart tissue with multiple small volumes of conductive fluid 6.

For surgical atrial fibrillation therapy, the hand-held jet injector 2 can be used to infuse the conductive fluid 6 in curvilinear patterns where the ablation electrodes 48 (described in more detail below) will be placed. For example, 50 microliters of 10% saline (by weight) could be injected into the left atrial epicardium 32 to achieve penetration depths of up to about 3 mm at injection point to injection point intervals of about 0.5 cm.

To create an encircling pattern corresponding to the ablation pattern around the right or left set of pulmonary veins would require about 30 to 40 injections of the conductive fluid 6 into left atrial epicardium 32 over a time period of about 60 to 120 seconds. Other desired lesions of shorter lengths could be done more quickly. It should be noted that the total volume injected can be quite small, less than a milliliter required for all lesions normally created in the left atrium. With such small volumes of injectate required, KCl in a concentration of 2 mEq/ml could safely be used as the conductive fluid 6 instead of 10 percent saline.

In one preferred aspect of the invention, hypertonic saline is preferred as the conductive fluid 6. For example, a volume of 10% saline (by weight) sufficient to attain a 5% volume concentration of the hypertonic saline within the tissue decreases the electrical resistivity of heart tissue from about 500 ohm-cm to about 100 ohm-cm provided that the injected saline is well distributed within the heart tissue. With respect to fat tissues, a well distributed injection of hypertonic saline sufficient to attain a 5% volume concentration of hypertonic saline would result in a tissue resistivity of about 110 ohm-cm which is about a ten-fold reduction of the normal tissue resistivity of fat. While hypertonic saline is preferred, the concentration of saline can vary from normal (about 0.9% by weight) to saturated saline solutions.

Other conductive fluids 6, however, can be used in place of saline solution. One conductive fluid 6 is potassium chloride (KCl). A standard concentration of KCl in 50 ml bottles is 2 mEq/ml (2 M). In heart tissue areas where 2 M KCl displaces at least one percent of tissue volume, the tissue remains in electrical diastole, and the heart muscle can not conduct a depolarization wavefront. The detection of a conduction block could be a means of determining that the conductive fluid 6 is well distributed into the desired tissue volume. Another conductive fluid 6 is sodium bicarbonate (NaHCO$_3$). A standard concentration of NaHCO$_3$ in 50 ml bottles is about 0.8 mEq/ml (0.8 M).

In one preferred embodiment, the conductive fluids 6 are very hypertonic, and could damage or even kill tissue directly. For ablation applications, however, this is not a problem since the intent of the procedure is to kill the tissue. For thinner layers of tissue, the injectate (i.e., the conductive fluid 6 that is injected) itself may be sufficient to form a transmural lesion without heating the tissue with RF energy. Table 1 lists possible conductive fluids 6 that could be used with the hand-held jet injector 2. Most of the conductive fluids 6 in Table 1 are solutions that are typically used for intravenous injections, or, as in the case with KCl, are injectable solutions available in the operating room. Since these conductive fluids 6 are biocompatible, their diffusion away from the injection site in the small quantities indicated is not dangerous to the general health of the patient.

TABLE 1

| AGENT | CHEMICAL FORMULA | CONCENTRATION |
|---|---|---|
| Sodium chloride | NaCl | 0.9–22% wt/volume |
| Potassium chloride | KCl | 0.5–2.0 Molar |
| Sodium bicarbonate | NaHCO$_3$ | 0.2–1.0 Molar |
| Ionic radiographic contrast material (Renografin ® 60) | Diatrizoate sodium Diatrizoate Meglumine | 50% wt/volume |
| Sodium citrate | Na$_3$C$_6$H$_5$O$_7$ | 0.5–2.0 Molar |
| Potassium citrate | K$_3$C$_6$H$_5$O$_7$ | 0.5–2.0 Molar |

The preferred embodiment is described in the context of using a conductive fluid 6 for the injectate. This description, however, is not intended to limit the injectate to conductive fluids 6. Other solutions, such as, for example, chemicals used to treat cancer cells can be used in the hand-held jet injector 2 described herein. The solution selected depends on the specific treatment to be administered.

Figure 3A:
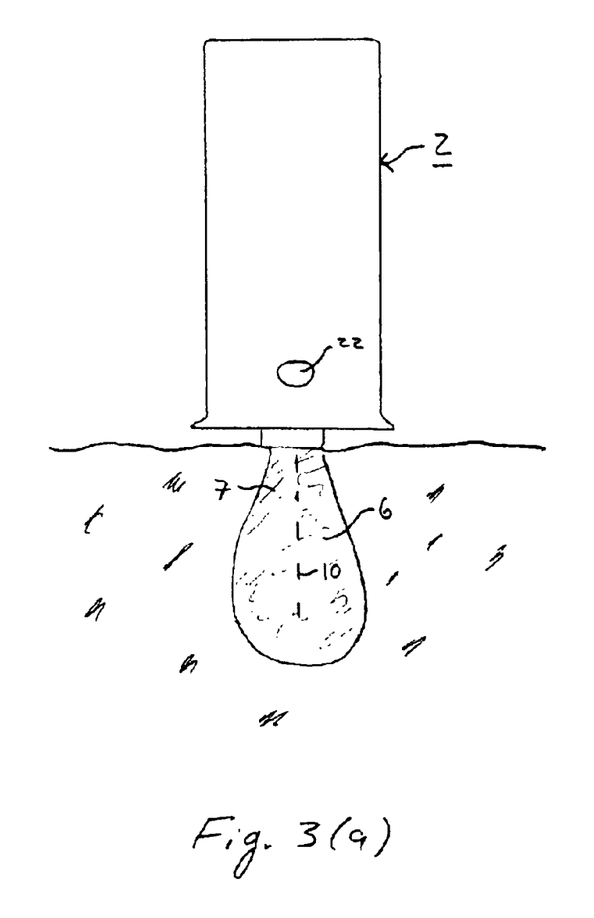
FIG. 3(a) shows a needleless hand-held jet injector injecting a conducting fluid into a region of tissue.
Figure 3B:
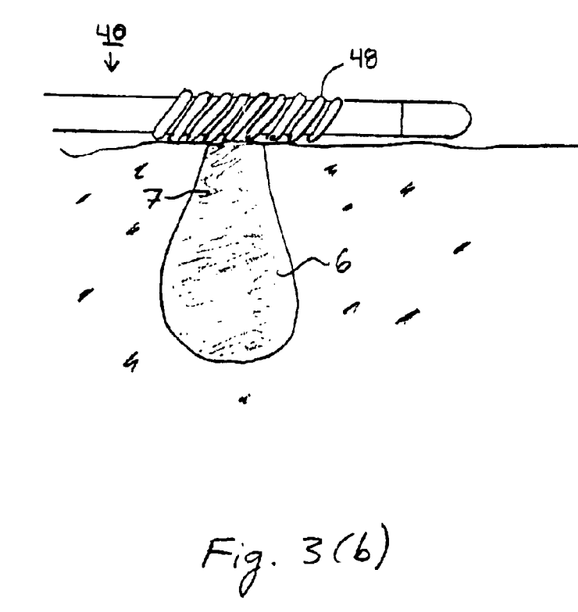
FIG. 3(b) shows an electrode of a probe positioned adjacent to the saline-injected region of tissue shown in FIG. 3(a).

In still another embodiment, a biocompatible dye 7 (shown in FIGS. 3(a) and 3(b)) can be added to the conductive fluid 6 to provide a means for tracking the location of the injection pattern. The dye 7 assists the operator by providing visual confirmation that the injection sites are sufficiently close to one another to promote uniformly deep lesions. If the physician performing the ablation procedure notices a gap in the injection pattern, the gap can be filled in with additional injections. The dye 7 can also be used to determine if the injectate volume is properly distributed in the tissue.

In situations where fluoroscopy is available, it may be desirable to document the pattern of the applied lesion using radiographic images. Radiographic contrast materials can be added to the conductive fluid 6 to show lesion location. Since non-ionic radiographic contrast materials are not very conductive and, thus, would not be very effective for this application, an ionic radiographic contrast material should be used in the injectate, such as, for example, RENOGRAFIN®.

Figure 2:
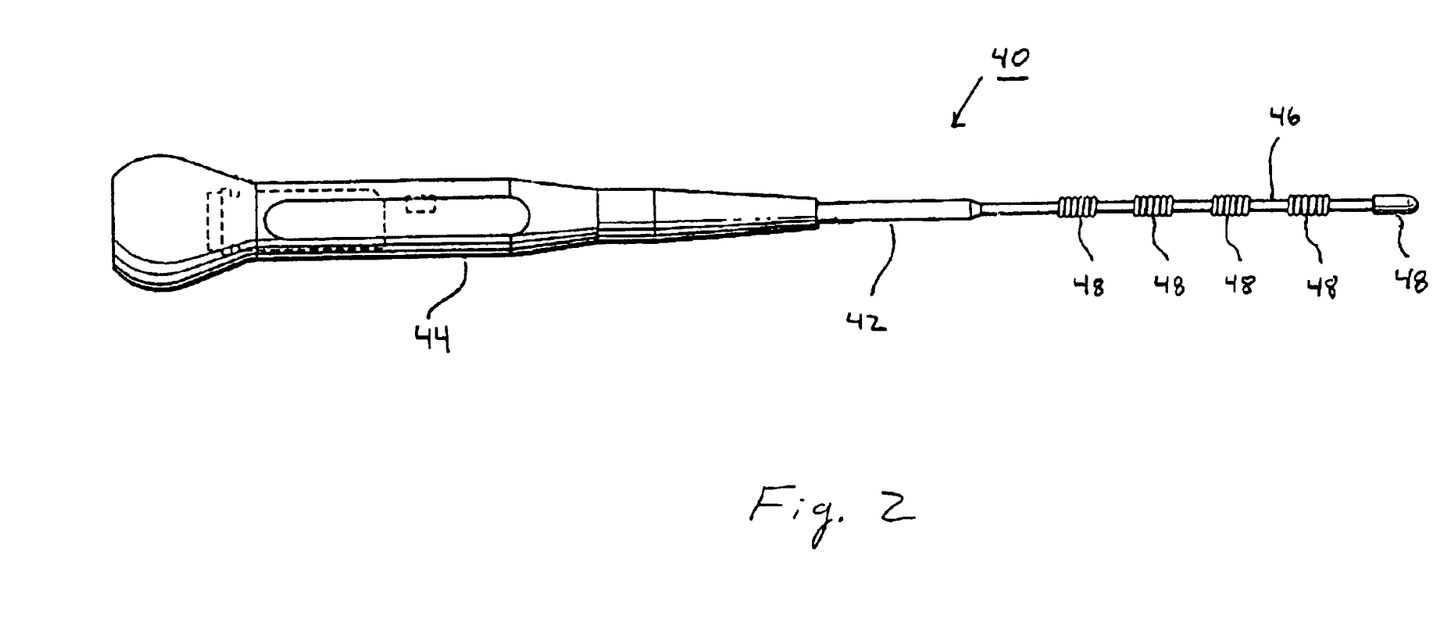
FIG. 2 illustrates a probe used to apply RF energy to a region of tissue.

After the heart tissue 32 has undergone pre-treatment by injecting conductive fluid 6, a separate probe 40 or the like is used to ablate the tissue using conventional RF ablation techniques. As seen in FIG. 2, the probe 40 typically includes a shaft 42, a handle 44, and a distal section 46. The distal section 46 contains a plurality of electrodes 48 that are coupled to a RF generator (not shown). During operation of the probe 40, one or more of the electrodes 48 is placed adjacent to an area of tissue (for example, as shown in FIG. 3(b)) that has been injected with conductive fluid 6.

Because the resistivity of the tissue has been reduced to such a degree by injection of the conductive fluid 6, a much higher power level can be applied to the ablation electrodes 48, thereby resulting in deeper lesions. For example, if sufficient conductive fluid 6 is injected to reduce tissue resistivity to about 100 ohm-cm in the most superficial 2 mm of tissue, the percent of power dissipation in that tissue layer is reduced from 50% to 20% of the applied power if ablating over muscle. If ablation is applied over fat, the power dissipation is applied over fat, the power dissipation in that 2 mm layer of tissue is reduced from 75% to 20% of applied power.

Moreover, if the RF electrode 48 is not actively cooled, the hottest tissue temperatures are at the electrode-tissue interface. RF power can effectively be controlled using a temperature feedback system based on measured temperature readings from temperature sensors (not shown) that are located adjacent to the electrodes 48. The combination of high-pressure conductive fluid 6 injection and RF ablation (non-active cooled) is able to create very deep and accurate lesions while also minimizing perforation risk. In another embodiment, the high pressure injection of conductive fluid 6 is combined with actively cooled RF ablation. The method is similar to that described above with the exception that an actively cooled probe 40 is used to cool the RF electrodes 48. This cooling can be accomplished using saline infusion around the electrodes to dissipate heat, or alternatively, the probe 40 can employ an internal-flow cooling mechanism. The combination of the injection technique described herein with cooled RF ablation is able to create even larger lesions.

FIGS. 3(a) and 3(b) graphically illustrate the two step process used to create accurate and deep lesions in tissue. First, as is shown in FIG. 3(a), the tissue region of interest is subject to high pressure needleless injection of a conductive fluid 6. The conductive fluid 6 penetrates into the tissue (between about 2 mm to about 5 mm) to saturate the region of interest. Next, a probe 40 or the like having RF ablation electrodes 48 is maneuvered into position so as to place an electrode 48 adjacent to the now injected site. When the probe 40 or other device is in position, RF power is delivered to the electrode 48 so as to heat the tissue to create a lesion. Preferably, RF ablation is started within a few minutes of completing the injection steps because injection of a hypertonic conductive fluid 6 will result in an increase in tissue water content over time.

With respect to the injection step, it is preferred to have a fairly tight distribution of conductive fluid 6 (cross section within the range of about 2 mm to about 5 mm) that extends transmurally to reduce the width of the resulting lesion. This may require two separate injections of conductive fluid 6 at two different pressures. A first higher pressure would be used to penetrate deep within a tissue and a second lower pressure would be used to saturate the tissue near the surface. Alternatively, a pressure waveform could be used that makes a deep penetrating pattern during the early part of the infusion cycle and a less penetrating pattern later in the infusion cycle. A dye 7 can be used to monitor whether the conductive fluid 6 is properly distributed in the tissue.

While FIGS. 1 and 3(a) show a hand-held jet injector 2 with a single nozzle 8, additional nozzles 8 can be provided to produce multiple jets 10 of conductive fluid 6. The nozzles 8 can be selected to produce the desired dispersion pattern within the tissue.

While a specific preferred hand-held jet injector 2 has been disclosed, other hand-held jet injectors 2 can also be used. All that is required is that the hand-held jet injector 2 be able to use high pressure to inject a conductive solution 6 into heart tissue to a depth of about 2 mm to about 5 mm without penetrating the tissue with a needle. For example, the power injectors used to inject radiographic contrast material into veins and arteries commonly found in hospitals can potentially be used to deliver conductive solution 6 to a region of tissue. These injectors are capable of generating pressures within the range of about 1000 psi to about 2000 psi.

In some operations, a hand-held jet injector 2 is the device of choice. However, for less invasive procedures, it is desirable to integrate the high pressure jet injection system with a probe 60 or catheter 100. These devices and their modes of operation are described in more detail below.

Figure 4:
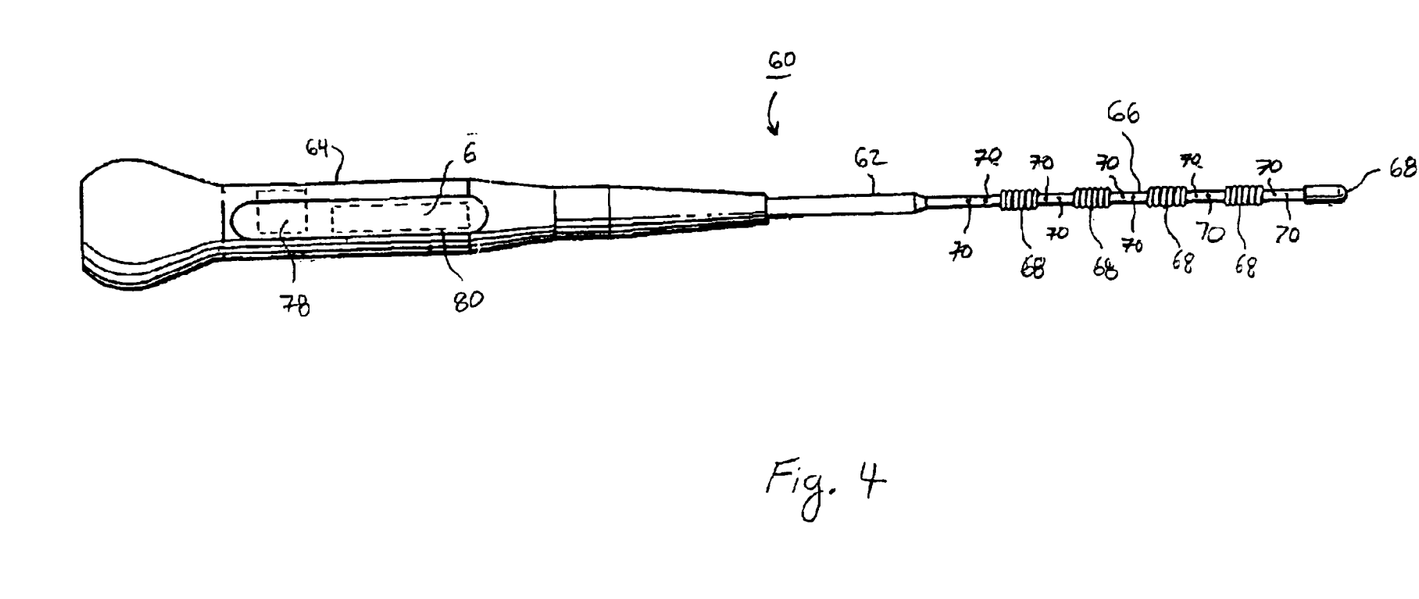
FIG. 4 is a side view of a RF probe device having a plurality of injection ports.
Figure 5:
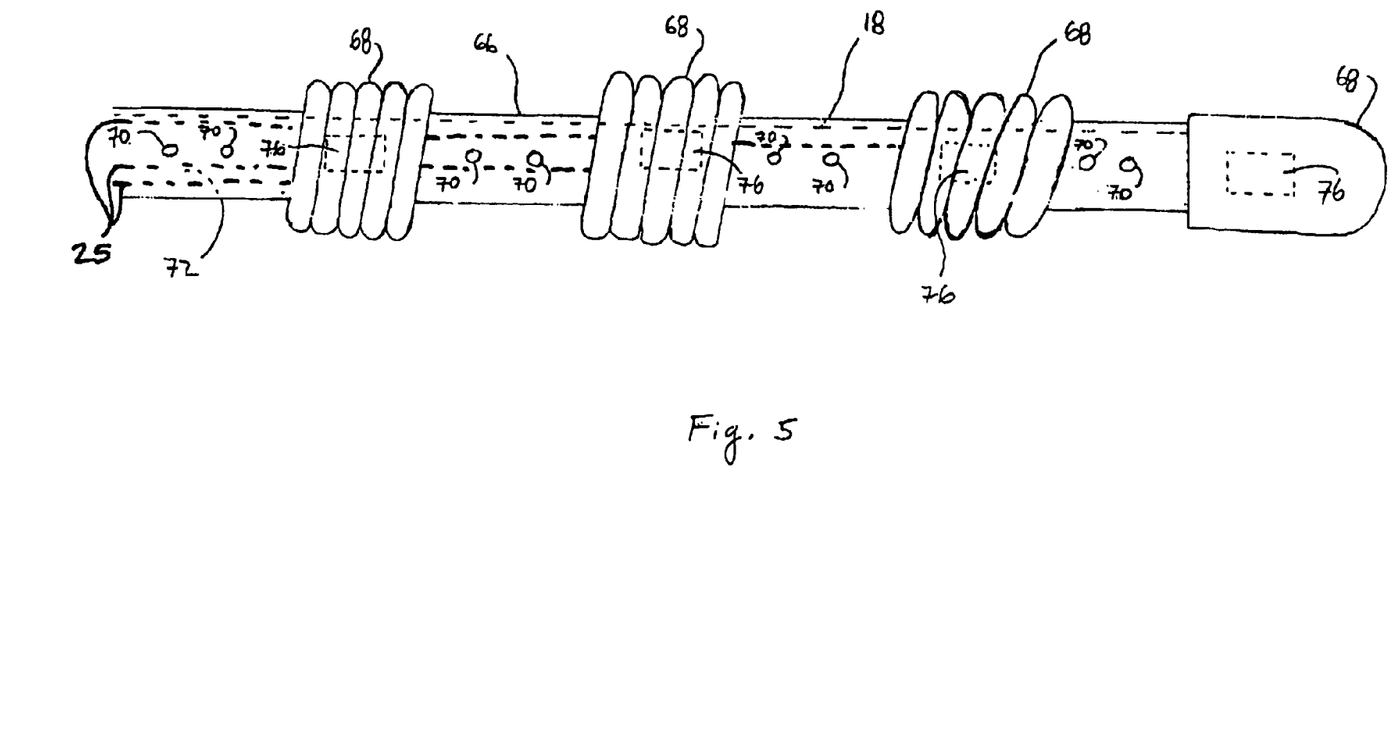
FIG. 5 is an enlarged view of the distal tip of the RF probe device shown in FIG. 4.

Referring to FIGS. 4 and 5, surgical probe 60 is shown in accordance with one preferred embodiment of the present invention. The surgical probe 60 is used to pre-treat tissue with a conductive fluid 6 as well as provide RF energy to the infused site. The probe 60 typically includes a shaft 62, a handle 64, and a distal section 66. The distal section 66 contains a plurality of electrodes 68 that are electrically coupled to a separate RF generator (not shown).

Located on the distal section 66 of the probe are a plurality of ports 70 (i.e., holes). The ports 70 are used to deliver a high pressure injection of conductive fluid 6 to a region of tissue. The ports 70 are preferably oriented along one side of the distal section 66 of the probe 60. The size and orientation of the ports 70 on the probe 60 depend on the length of the probe 60 and the number of electrodes 68 contained thereon.

Figure 6:
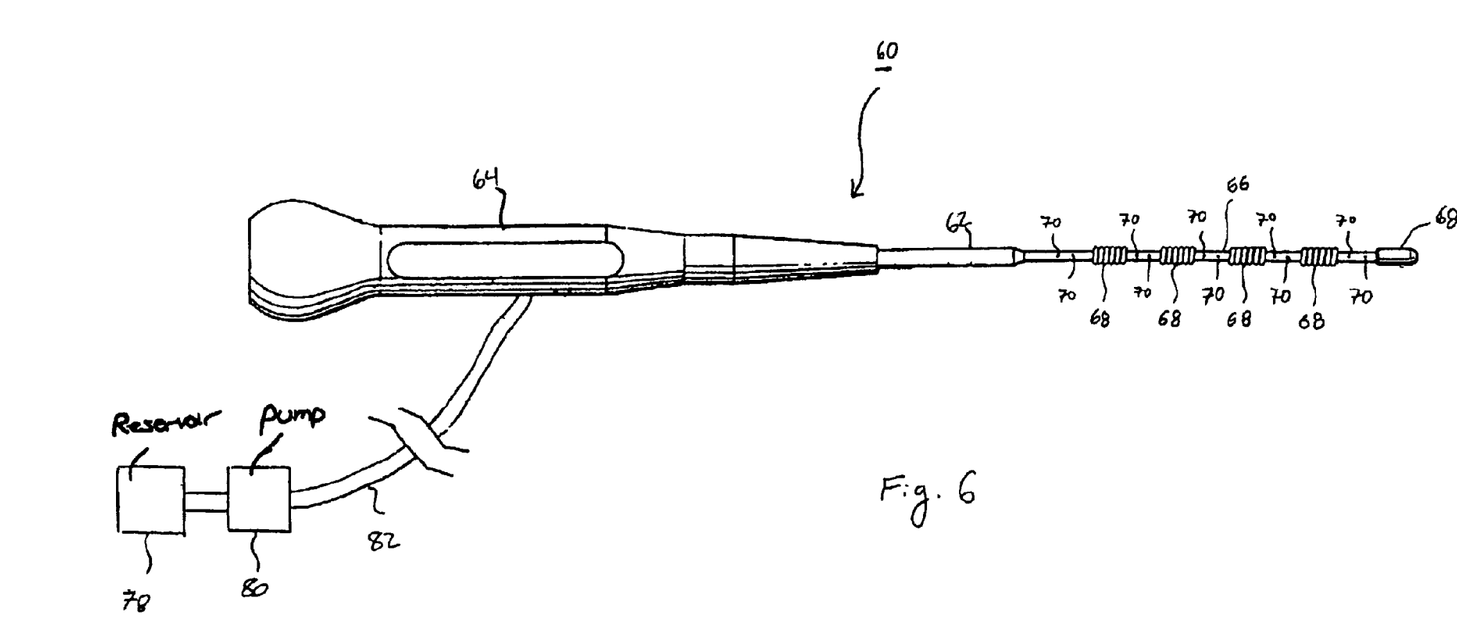
FIG. 6 is a side view of a RF probe device having an external pumping mechanism and reservoir.
Figure 7:
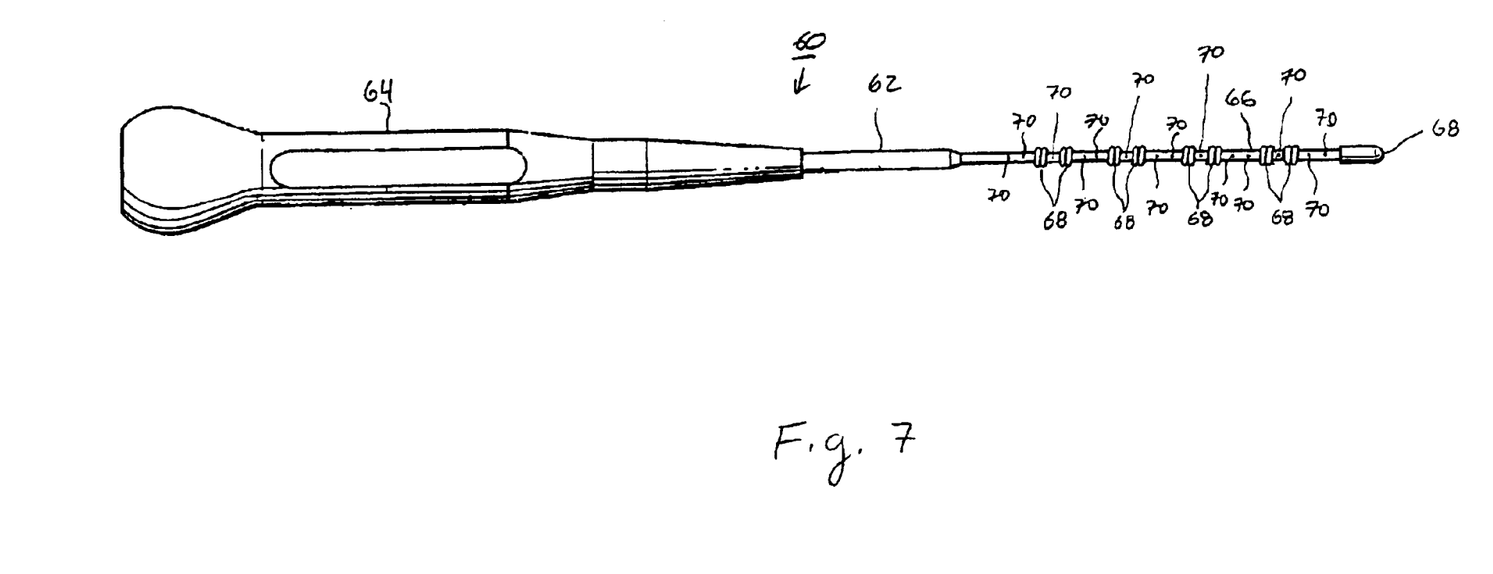
FIG. 7 is a side view of a RF probe device according to an alternative embodiment of the invention.

It is preferable to have the ports 70 located as close as possible to the electrodes 68. FIGS. 4 through 6 illustrate one preferred embodiment wherein the ports 70 are located in the distal section 66 between adjacent electrodes 68. FIG. 7 illustrates another embodiment wherein at least one port 70 is located substantially in the center of each coiled electrode 68. For a typical probe 60 having a length of 10 cm, about ten to about twenty ports 70 are preferably disposed on the probe 60. It should be understood, however, that the number of ports 70 can vary outside of this range and still fall within the scope of the invention.

In a preferred aspect of the invention, the distal section 66 of the probe 60 is formed from stainless steel hypotube. The internal diameter of the hypotube falls within the range of about 0.010" to about 0.025". The ports 70 are preferably laser-drilled in the side of the hypotube and have diameters within the range of about 0.002" to about 0.004".

As seen in FIG. 5, the distal section 66 of the probe 60 includes a lumen 72 for carrying conductive fluid 6 therein. The lumen 72 is in fluid communication with the ports 70 of the probe 60. FIG. 5 also shows RF energy conductors 25 separate ones of which electrically connect to each electrode 68. The RF energy conductors 25 provide a means to separately control electrical current to each electrode 68. The RF energy conductors 25 reside within a lumen separates from the lumen 72 that carries conductive fluid 6 (to prevent a short-circuit) between electrodes 68. The RF conductors 25 are connected to a separate ablation controller (not shown) that generates and supplies the probe 60 with RF energy.

Each electrode 68 is preferably associated with a temperature sensor 76 (as shown in FIG. 5). The temperature sensor 76 can be located, for example, between the hypotube and the coiled electrodes 68. The temperature sensors 76 are oriented on the same side of the probe 60 as the ports 60. The temperature sensors 76 can include any number of types of sensors such as, for example, thermocouples, thermistors, and digital IC temperature sensors. The temperature sensors 76 are used to monitor tissue temperature during RF ablation. The temperature sensors 76 can also be coupled to associated control circuitry in a feedback arrangement to provide for control of the amount of RF power delivered to the tissue.

In one aspect of the invention, the conductive fluid 6 is stored within a reservoir 78 contained within the handle 64 portion of the probe 60. In addition, a pumping mechanism 66 is also provided in the handle portion 64. The pump 80 provides conductive fluid 6 to the lumen 72 of the hypotube at high pressure (i.e., a source of pressurized conductive fluid 6). Alternatively, the reservoir 78 and pumping mechanism 80 can be located external to the probe 60. For example, FIG. 6 illustrates an embodiment wherein tubing 82 connects the probe 60 to an external pump 80 and reservoir 78.

Figure 9B:
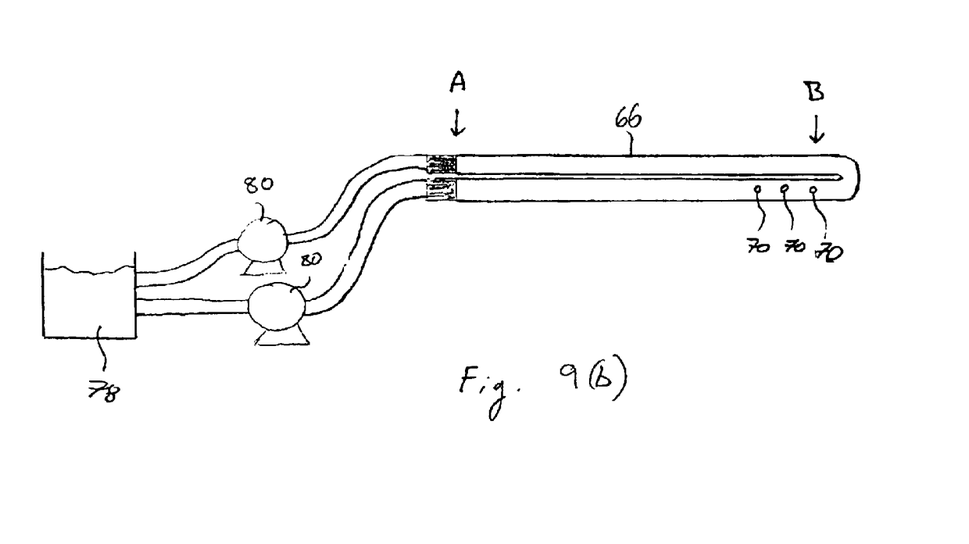
FIG. 9(b) is a schematic view of an alternative RF probe device wherein both ends of the probe are pressurized.
Figure 9C:
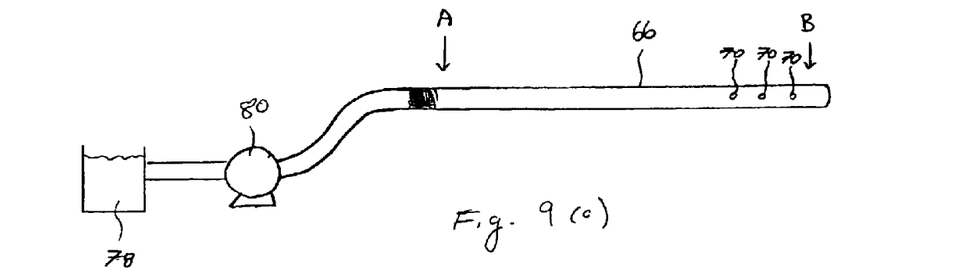
FIG. 9(a) is a schematic view of a RF probe device shown connected to a pumping mechanism and a reservoir.
Figure 11A:
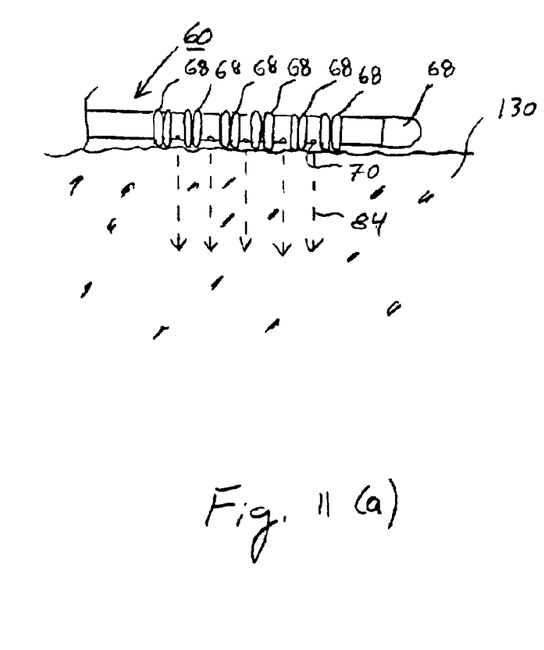
FIG. 11(a) shows a RF probe adjacent to a region of heart tissue that is injecting a jet of conductive fluid into the tissue.

The pumping mechanism 80 preferably creates a high pressure within the lumen 72 of the distal section 66 of the probe 60 that ejects a narrow stream of injectate 84 (as shown, for example, in FIG. 11(a)) out of the ports 70. Preferably, the pressure within the lumen 72 at each port 70 is within the range of about 500 psi to about 1500 psi. Because the lumen 72 of the probe 60 is so narrow, a substantial pressure drop is created along the length of the probe 60. For example, as shown in FIG. 9(a), a substantial pressure drop is created between points A and B of the probe 60. The pressure required in the proximal end of the lumen 72 needs to be high enough to produce injection pressures within the range of about 500 psi to about 1500 psi at the ports 70. Preferably, the pressure in the proximal end of the lumen 72 is within the range of about 1000 psi to about 2000 psi. To reduce the pressure drop along the length of the probe 60, the hypotube can be made into a loop with both ends of the loop being pressurized. This alternative embodiment is schematically illustrated in FIG. 9(b).

Figure 8:
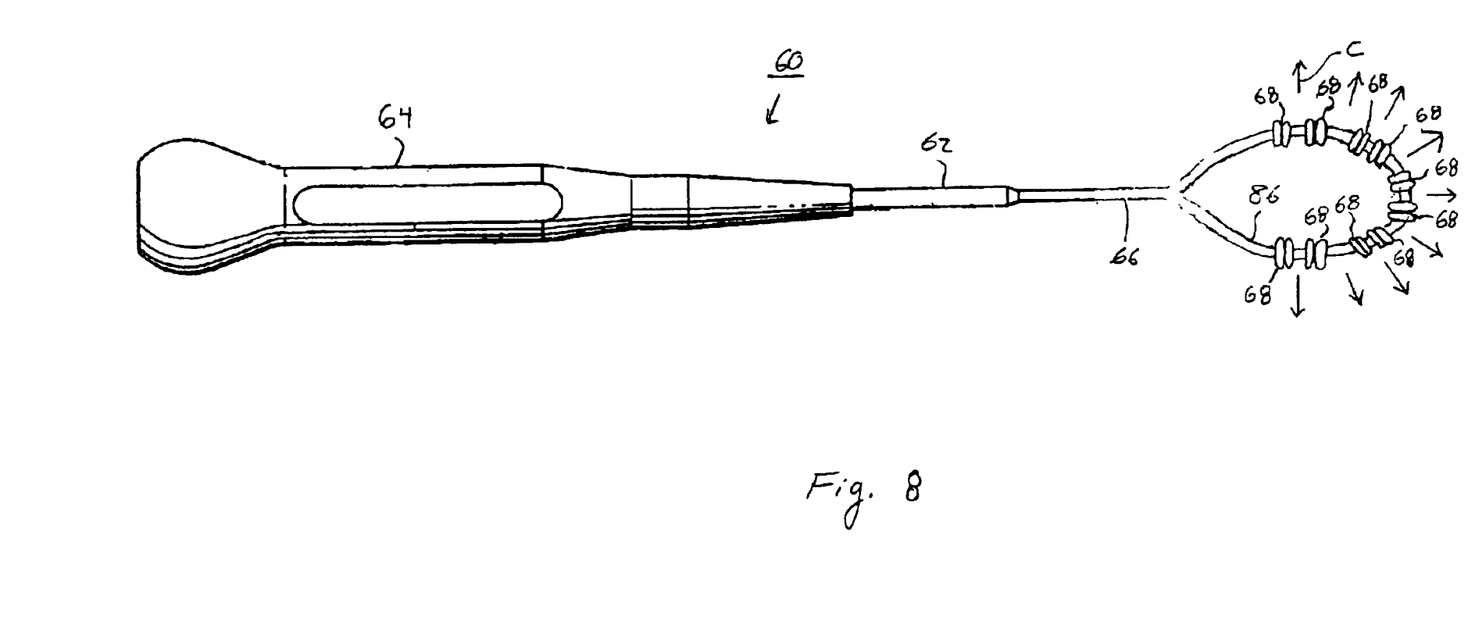
FIG. 8 is a side view of a RF probe device according to yet another alternative embodiment of the invention.

FIG. 8 illustrates an alternative embodiment of the probe 60. In this embodiment, the distal section 66 of the probe 60 terminates in a loop section 86. Preferably, this loop section 86 is flexible and can lie flat against tissue when appropriate pressure is applied to the probe 60. Arrows C indicate the direction of travel for the injectate 84.

The amount of pressure required in the probe 60 or catheter 100 depends on the desired depth of penetration and the type of tissue that is being treated. Preferably, the probe 60 or catheter 100 produces a narrow jet of injectate 84 (as shown in FIG. 11(a)) at a sufficient speed to penetrate heart tissue to a depth within the range of about 2 mm to about 5 mm. For example, fatty tissue is relatively easy to penetrate and would require lower pressures than muscle tissue. It is preferable that the operator can control the pressure that is delivered via the probe 60 or catheter 100. This pressure can be input to the device using commonly known mechanical or electronic control techniques.

Figure 10:
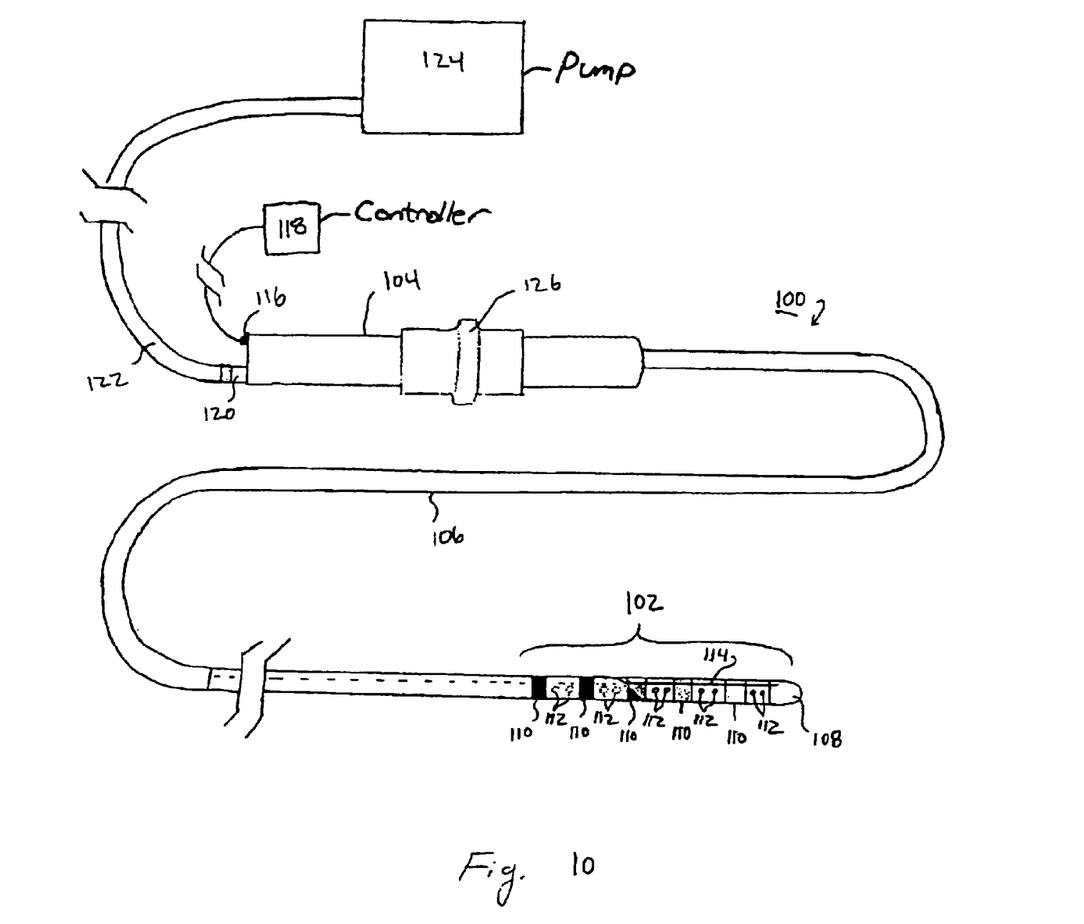
FIG. 10 is a schematic view showing a RF ablation catheter according to one aspect of the invention.

The present invention also has application in catheters such as the exemplary catheter 100 shown in FIG. 10. The catheter 100 includes a distal electrode segment 102 and a proximal handle 104 that are connected by a torquable catheter shaft 106. The catheter shaft 106 includes a lumen therein (not shown) for the passage of conductive fluid 6. The electrode segment 102 houses the tip electrode 108 and a plurality of ring electrodes 110. Temperature sensors (not shown) are provided adjacent to the electrodes 108, 110. The distal electrode segment 102 includes a plurality of ports 112 that allow fluid communication from the lumen inside the catheter 100 to the outside environment. As with the probe 60 embodiment, the ports 112 preferably have diameters within the range of about 0.002" to about 0.004." The ports 112 may be produced, for example, by drilling with a laser.

FIG. 10 also shows a RF conductor 114 passing through the catheter 100 that is also electrically connected to each electrode 108, 110. The proximal end of the RF conductor 114 is coupled at the handle 104 via electrical connector 116 to a RF controller 118. The RF controller 118 includes a RF generator that generates the RF energy needed at each electrode 108, 110.

The handle 104 also includes a fitting 120, such as a Leur fitting 120 that connects to tubing 122 that, in turn, connects to a pump 124. The pump 124 preferably contains a reservoir for storing conductive fluid 6. Alternatively, the pump 124 can be connected to a separate source of conductive fluid 6. The handle 104 includes a knob 126 that is used to deflect the distal tip of the catheter 100. Pulling the knob 126 away from the catheter shaft 106 causes the tip to deflect. Pushing the knob 126 towards the catheter shaft 106 straightens the tip of the catheter 100. Rotation of the handle 104 to the right and left rotates the catheter tip in either direction. While one preferred steering mechanism has been disclosed herein, it should be understood that any commonly known steering mechanisms can be used to control the catheter 100.

The above-described catheter 100 preferably uses a single lumen to deliver the conductive fluid 6 to the ports 112. However, a dual lumen approach similar to that shown in FIG. 9(b) with respect to the probe 60 may also be used.

Figure 11B:
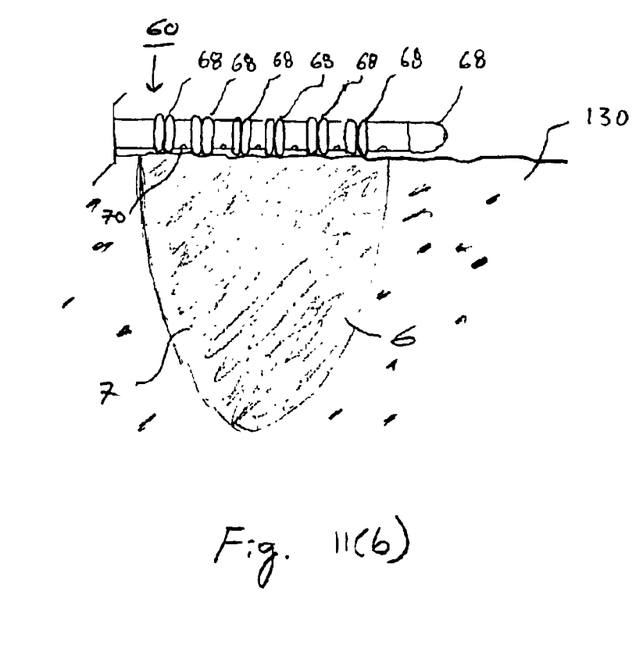
FIG. 11(b) shows the RF probe of FIG. 11(a) after the tissue has been injected with the conductive solution.

In a preferred embodiment of the invention, the probe 60 and catheter 100 are used to pre-treat human heart tissue 130 (as shown in FIGS. 11(a) and 11(b) prior to RF ablation for the treatment of tachycardia. If the probe 60 is used, the tachycardia treatment is performed after a surgical operation such as a mini-thoracotomy is performed to allow access to a surface of a human heart 30. If a catheter 100 is used, the catheter 100 is advanced intravascularly, for example, through the femoral artery. After access to the heart 30 has been established, the next step employs a combined jet injection/RF ablation device (either the probe 60 or the catheter 100) to prepare the heart tissue by injecting the tissue with a narrow jet 84 of conductive fluid 6. With respect to the probe 60, injection is preferably accomplished by resting the probe 60 adjacent to the tissue of interest. For the catheter 100, the distal electrode segment 102 is positioned adjacent to the tissue of interest. Importantly, there are no needles that penetrate the tissue of the heart 30.

Some procedures may require a single burst or a single sustained injection of conductive fluid 6. In other procedures, however, it may be advantageous to inject the heart tissue with multiple small volumes of conductive fluid 6.

Similar to the hand-held jet injector 2 embodiment, the probe 60 and catheter 100 may be used with the same conductive fluids that are disclosed above. Similarly, biocompatible dyes 7 and radiographic contrast materials can be added to the conductive solution.

The probe 60 and catheter 100 can use a temperature feedback system similar to that disclosed with respect to the probe 40 to control RF power while maintaining tissue temperatures below 100° C. In addition, the probe 60 and catheter 100 may be actively cooled to further increase the lesion depth. This cooling can be accomplished using saline infusion around the electrodes 68, 110 using ports 70, 112 to dissipate heat or, alternatively, the probe 60 or catheter 100 can employ an internal-flow cooling mechanism. The combination of a cooled probe 60 or catheter 100 with the jet injection method described herein is able to create very deep lesions.

With respect to the injection step using the probe 60 or catheter 100, it is also preferred to have a fairly tight distribution of conductive fluid 6 (cross section within the range of about 2 mm to about 5 mm) that extends transmurally to reduce the width of the resulting lesion. This can be accomplished in two separate injections or a single injection having a particular pressure waveform as is described in more detail above.

The choice of what injection device to use (i.e., the hand-held jet injector 2, the probe 60, or catheter 100) depends on a number of factors including, but not limited to, the location of the heart tissue of interest, the nature of the tachycardia (atrial or ventricular, for example), as well as the access route chosen to reach the tissue of interest.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A method for treating tissue comprising the steps of:
   providing an injecting device adjacent to a portion of the tissue;
   injecting the tissue with a jet of conductive fluid to a depth within the range of about 2 mm to about 5 mm; and
   applying RF energy to the tissue containing the injected conductive fluid.

2. The method according to claim 1, wherein the step of injecting is performed at a pressure within the range of about 500 psi to about 1500 psi.

3. The method according to claim 1, wherein the conductive fluid is a solution selected from the group consisting of sodium chloride, potassium chloride, sodium bicarbonate, sodium citrate, and potassium citrate.

4. The method according to claim 1, wherein the conductive fluid comprises an ionic radiographic contrast material.

5. The method according to claim 1, wherein the conductive fluid contains a dye.

6. The method according to claim 1, wherein the injection device is a hand-held jet injector.

7. The method according to claim 1, wherein the injection device is a probe.

8. The method according to claim 1, wherein the injection device is a catheter.

9. The method according to claim 1, wherein the step of injecting the tissue and the step of applying RF energy to the injected tissue are performed by a single probe.

10. The method according to claim 1, wherein the step of injecting the tissue and the step of applying RF energy to the injected tissue are performed by a single catheter.

11. The method according to claim 1, wherein after application of the RF energy a lesion is formed having a depth of with the range of about 1 mm to about 10 mm.

12. The method according to claim 1, wherein the jet of conductive fluid is injected to a tissue depth of up to about 3 mm.

13. The method according to claim 1, wherein the tissue is myocardial tissue.

14. The method according to claim 1, wherein the tissue is ablated by the RE energy.

15. A method for treating tissue comprising the steps of:
    injecting the tissue with a jet of conductive fluid to a depth within the range of about 2 mm to about 5 mm; and
    applying RE energy to the tissue containing the injected conductive fluid.

16. The method according to claim 15, wherein the step of injecting is performed at a pressure within the range of about 500 psi to about 1500 psi.

17. The method according to claim 15, wherein the conductive fluid is a solution selected from the group consisting of sodium chloride, potassium chloride, sodium bicarbonate, sodium citrate, and potassium citrate.

18. The method according to claim 15, wherein the conductive fluid comprises an ionic radiographic contrast material.

19. The method according to claim 15, wherein the conductive fluid contains a dye.

20. The method according to claim 15, wherein the step of injecting the tissue and the step of applying RF energy to the injected tissue are performed by a single probe.

21. The method according to claim 15, wherein the step of injecting the tissue and the step of applying RF energy to the injected tissue are performed by a single catheter.

22. The method according to claim 15, wherein after application of the RF energy a lesion is formed having a depth of with the range of about 1 mm to about 10 mm.

23. The method according to claim 15, wherein the jet of conductive fluid is injected to a tissue depth of up to about 3 mm.

24. The method according to claim 15, wherein the tissue is myocardial tissue.

25. The method according to claim 15, wherein the tissue is ablated by the RE energy.

* * * * *